(12) United States Patent
Surti

(10) Patent No.: US 9,913,574 B2
(45) Date of Patent: Mar. 13, 2018

(54) ENDOSCOPE CAP WITH RAMP

(75) Inventor: Vihar C. Surti, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 365 days.

(21) Appl. No.: 12/968,810

(22) Filed: Dec. 15, 2010

(65) Prior Publication Data

US 2011/0152618 A1    Jun. 23, 2011

Related U.S. Application Data

(60) Provisional application No. 61/288,050, filed on Dec. 18, 2009, provisional application No. 61/288,259, filed on Dec. 18, 2009, provisional application No. 61/288,060, filed on Dec. 18, 2009.

(51) Int. Cl.
| | |
|---|---|
| *A61B 1/00* | (2006.01) |
| *A61B 1/018* | (2006.01) |
| *A61B 1/012* | (2006.01) |
| *A61M 25/00* | (2006.01) |

(52) U.S. Cl.
CPC .......... *A61B 1/012* (2013.01); *A61B 1/0008* (2013.01); *A61B 1/0014* (2013.01); *A61B 1/00089* (2013.01); *A61B 1/00098* (2013.01); *A61B 1/00101* (2013.01); *A61B 1/00135* (2013.01); *A61B 1/00137* (2013.01); *A61B 1/018* (2013.01); *A61M 25/0067* (2013.01)

(58) Field of Classification Search
CPC .............. A61B 1/0008; A61B 1/00098; A61B 1/00101; A61B 1/0014; A61B 1/018; A61B 1/2736; A61B 2017/003; A61B 2017/0034; A61B 2017/2905; A61B 2017/2908; A61B 1/00089; A61B 1/00137; A61M 25/0026; A61M 25/0032; A61M 25/0067; A61M 25/0071; A61M 25/003

USPC ....... 600/106, 107, 121, 125, 127, 129, 153, 600/585; 606/191; 604/103.4, 604/95.01–95.05

See application file for complete search history.

(56) References Cited

U.S. PATENT DOCUMENTS

| | | | | |
|---|---|---|---|---|
| 4,593,680 | A * | 6/1986 | Kubokawa | .................... 600/107 |
| 4,632,110 | A * | 12/1986 | Sanagi | .......................... 606/207 |
| 5,571,093 | A * | 11/1996 | Cruz et al. | .................... 604/270 |
| 6,352,503 | B1 * | 3/2002 | Matsui | .................... A61B 1/018 |
| | | | | 600/106 |
| 6,461,321 | B1 * | 10/2002 | Quinn | ............................. 604/43 |
| 6,605,033 | B1 | 8/2003 | Matsuno | |
| 6,689,051 | B2 | 2/2004 | Nakada et al. | |

(Continued)

FOREIGN PATENT DOCUMENTS

| | | |
|---|---|---|
| DE | 20 2008 007 774 U1 | 9/2008 |
| EP | 1 284 120 A1 | 2/2003 |

(Continued)

*Primary Examiner* — Timothy J Neal
*Assistant Examiner* — Aaron B Fairchild
(74) *Attorney, Agent, or Firm* — Brinks Gilson & Lione

(57) ABSTRACT

An endoscope cap is provided for directing medical devices toward a selected target anatomy in a patient. The endoscope cap includes a ramp that may be used to deflect medical devices that have been advanced from a proximal portion of an endoscope to a distal portion thereof. The ramp may be integral with the endoscope cap, or alternatively, may be pivotally attached thereto.

17 Claims, 14 Drawing Sheets

(56) References Cited

U.S. PATENT DOCUMENTS

| | | |
|---|---|---|
| 6,783,491 B2 * | 8/2004 | Saadat et al. ............... 600/114 |
| 7,347,860 B2 * | 3/2008 | Ouchi ............................ 606/46 |
| 8,602,970 B2 | 12/2013 | Muyari et al. |
| 2001/0000041 A1 * | 3/2001 | Selmon et al. ............... 600/585 |
| 2001/0049509 A1 | 12/2001 | Sekine et al. |
| 2002/0103424 A1 * | 8/2002 | Swoyer ............ A61B 5/04884 600/350 |
| 2002/0156344 A1 | 10/2002 | Pasricha et al. |
| 2002/0156347 A1 * | 10/2002 | Kim ................. A61B 1/00156 600/160 |
| 2003/0040657 A1 * | 2/2003 | Yamaya et al. ............... 600/107 |
| 2003/0088154 A1 | 5/2003 | Ishibiki et al. |
| 2004/0034369 A1 * | 2/2004 | Sauer et al. .................. 606/139 |
| 2004/0267092 A1 | 12/2004 | Ishibiki |
| 2005/0059890 A1 | 3/2005 | Deal et al. |
| 2005/0080411 A1 * | 4/2005 | Ouchi ............... A61B 18/1492 606/45 |
| 2005/0222495 A1 | 10/2005 | Okada et al. |
| 2005/0288549 A1 | 12/2005 | Mathis |
| 2006/0258910 A1 | 11/2006 | Stefanchik et al. |
| 2006/0264705 A1 | 11/2006 | Adams et al. |
| 2007/0142709 A1 | 6/2007 | Martone et al. |
| 2008/0177135 A1 | 7/2008 | Muyari et al. |
| 2009/0259172 A1 | 10/2009 | Yamaoka et al. |
| 2010/0113878 A1 | 5/2010 | Kawano |
| 2014/0066707 A1 | 3/2014 | Muyari et al. |

FOREIGN PATENT DOCUMENTS

| | | |
|---|---|---|
| EP | 1 582 138 A2 | 10/2005 |
| EP | 1 721 567 A2 | 11/2006 |
| JP | 10-99266 | 4/1998 |
| JP | 2003-245244 | 9/2003 |
| JP | 2004-209137 | 7/2004 |
| JP | 2005-253873 | 9/2005 |
| JP | 2005-287963 | 10/2005 |
| JP | 2008-173369 | 7/2008 |
| JP | 2008-536579 | 9/2008 |
| JP | 2008-272133 | 11/2008 |
| WO | WO 2006/113465 A1 | 10/2006 |
| WO | WO 2007/091523 A1 | 8/2007 |

* cited by examiner

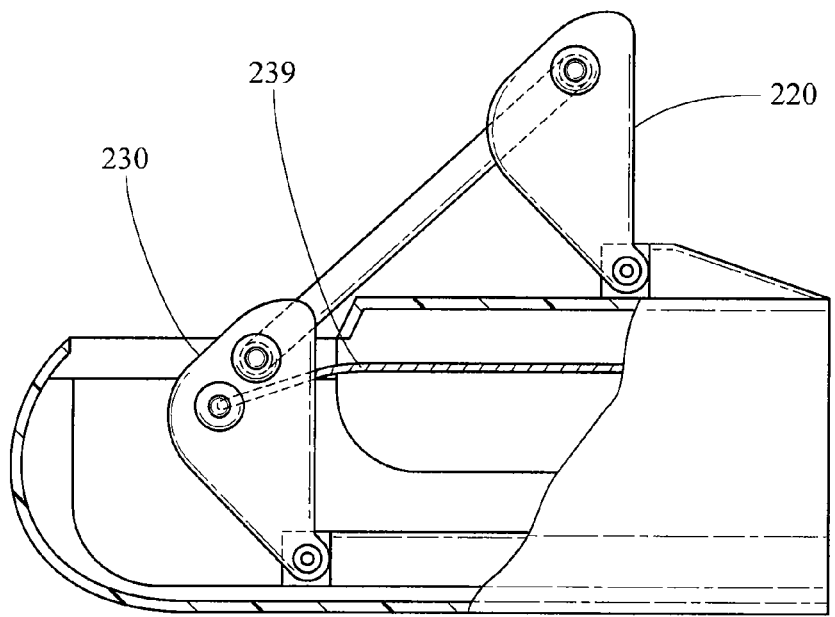
FIG. 2C
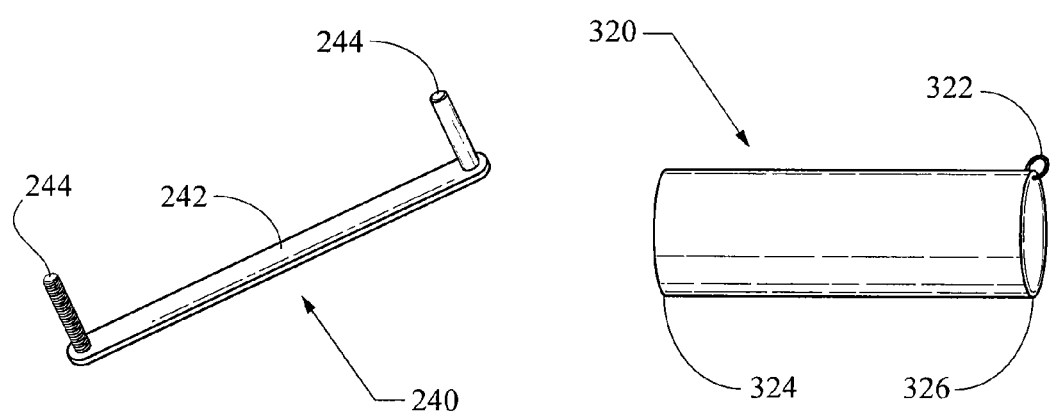
FIG. 2D
FIG. 3

ENDOSCOPE CAP WITH RAMP

CROSS-REFERENCE TO RELATED APPLICATIONS

The present application claims the benefit of the following applications: U.S. Provisional Application No. 61/288,050, titled "Endoscope Cap With Ramp", filed on Dec. 18, 2009, the entirety of which is hereby incorporated by reference; U.S. Provisional Application No. 61/288,259, titled "Advancing System and Method of Use Thereof", filed Dec. 18, 2009, the entirety of which is hereby incorporated by reference; and U.S. Provisional Application No. 61/288,060, titled "Endoscope Sheath", filed Dec. 18, 2009, the entirety of which is hereby incorporated by reference.

TECHNICAL FIELD

The present invention relates to medical devices, and more particularly to an endoscope cap with a ramp.

BACKGROUND OF THE INVENTION

Physicians use endoscopes during minimally invasive procedures to visualize the patient anatomy, diagnose various conditions, and deliver instrumentation to the treatment site. Devices are typically delivered via a working channel of the endoscope, which generally ranges from about 2.0 to 3.5 mm in diameter, and may be used to introduce catheters and other elongate devices, including forceps, scissors, brushes, snares, and baskets. Larger working channels of 5.0 mm in diameter are available in certain specialized endoscopes, and may be used to pass relatively large devices or provide capability for improved aspiration or decompression. Some devices, however, are simply too large to pass through available endoscopes. Moreover, the specialized endoscopes with larger working channels can be expensive, as well as difficult to intubate due to increased rigidity and outer diameter.

Devices too large for the endoscope working channel must be introduced through an alternate, and often more invasive procedure, such as laparoscopy or open surgery. Laparoscopic surgery involves creating 0.5-1.5 cm incisions in a patient's abdominal wall so that a laparoscope and other instruments can be introduced into the abdominal and pelvic cavities. Open surgery generally involves creating one or more long incisions in a patient, followed by extensive muscle stripping, prolonged retraction of tissues, denervation and devascularization of tissue. While effective at introducing larger devices, laparoscopic and open surgical procedures can increase the risk of complications and trauma to the patient, as well as extend recovery time and hospital stays.

What is needed are devices and methods for endoscopic introduction of medical devices too large for the endoscope working channel without necessitating the use of invasive procedures. Specifically, devices and methods are needed for introduction of medical devices alongside and external to an endoscope.

SUMMARY

The present disclosure generally provides a cap configured to attach to the distal end of an endoscope, preferably a duodenoscope. The cap may be used to aid in the delivery of devices to a selected target area in the anatomy of a patient. Preferably, the cap is used in conjunction with a system for advancing devices alongside an endoscope. Once a device reaches a distal portion of the endoscope, the cap may be used to deflect the device toward a selected target area, such as the pancreatic duct. In one embodiment, the cap can be used with a tether system used for pulling devices down alongside an endoscope. The tether system may include a guiding member for advancing devices beyond a distal portion of the endoscope. In another embodiment, the cap may be used in conjunction with a sheath system used for advancing devices down alongside an endoscope. In another embodiment, the cap, the tether, and the sheath may be used in combination.

In one aspect, an endoscope cap is provided for deflecting devices toward a selected target anatomy. The endoscope cap includes a body comprising a proximal end and a distal end. The endoscope cap also includes a first aperture disposed at the proximal end and configured to receive a distal portion of an endoscope. The endoscope cap further includes a first ramp disposed between the proximal end and the distal end. The first ramp projects outwardly from the body, and is configured to deflect a medical device disposed externally to the endoscope in a direction away from the endoscope. Preferably, the cap includes a second aperture disposed proximal to the distal end, and is configured to accommodate an aperture of a working channel of the endoscope.

In one embodiment, the first ramp is integral with the body.

In another embodiment, the first ramp is pivotally attached to the body and may pivot from a first configuration to a second configuration. The first ramp may include a first transverse passageway and a second transverse passageway disposed through the ramp. The endoscope cap may include a ramp turning support attached to the body and partially disposed through the first transverse passageway. The endoscope cap may include a second ramp disposed proximal to the first ramp and may be configured to direct a device toward the first ramp.

In one embodiment, the endoscope cap includes a coupling member configured to couple with an endoscope sheath lumen. Preferably, the endoscope sheath lumen is configured for advancing devices from a proximal portion of an endoscope to a distal portion of the endoscope. The coupling member may include a coupling member proximal portion and a coupling member distal portion. The coupling member may further include a coupling member lumen extending from the coupling member proximal portion to the coupling member distal portion. Preferably, the coupling member lumen is open at both ends and is aligned with the first ramp. The coupling member proximal portion may include an outer surface configured to frictionally engage an inner surface of the endoscope sheath lumen.

In another aspect, an advancing system is provided for advancing devices toward a selected target anatomy. The advancing system includes an endoscope having a proximal portion and a distal portion. The advancing system further includes an endoscope cap including a first ramp configured to engage and deflect an elongate device advanced along the exterior of the endoscope. The endoscope cap is disposed on the distal portion of the endoscope. The first ramp may be integral with the endoscope cap, or alternatively, may be pivotally attached thereto and may pivot from a ramp first configuration to a ramp second configuration. The advancing system may include a connecting member having a first attachment element and a second attachment element. The advancing system may include an elevator apparatus pivotally attached to the distal portion of the endoscope. Preferably, the elevator apparatus can pivot from an elevator first configuration to an elevator second configuration. The elevator apparatus may include first, second, and third transverse passageways disposed through the elevator apparatus. An elevator turning support may be attached to the distal portion of the endoscope and may be partially disposed through the first transverse passageway. The elevator apparatus may include an elevator wire disposed through the second transverse passageway, and the wire may be operatively connected at the proximal portion of the endoscope. The advancing system may include a fourth transverse passageway disposed through the first ramp, wherein the first attachment element is disposed in the third transverse passageway and wherein the second attachment element is disposed in the fourth transverse passageway. The advancing system may further include a second ramp disposed proximal to the first ramp and may be configured to direct a device toward the first ramp.

In another aspect, a method is provided for delivering a medical device to an internal site of treatment in a patient. The method uses an endoscope cap including a body comprising a proximal end and a distal end, a first aperture disposed at the proximal end and configured to receive a distal portion of an endoscope. The endoscope cap also includes a first ramp disposed between the proximal end and the distal end. The method includes advancing a device to a distal portion of the endoscope, advancing the device onto the first ramp, and advancing the device off of the first ramp toward a selected target anatomy.

Other systems, methods, features and advantages will be apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The system may be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIGS. 2A-2C depict endoscope cap 100 with a pivotally attached ramp 220.

FIG. 2D depicts connecting member 240.

FIG. 3 depicts medical device 320.

DEFINITIONS

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The present invention also contemplates other embodiments "comprising," "consisting of" and "consisting essentially of," the embodiments or elements presented herein, whether explicitly set forth or not.

The term "biocompatible," as used herein, refers to a material that is substantially non-toxic in the in vivo environment of its intended use, and that is not substantially rejected by the patient's physiological system. A biocompatible structure or material, when introduced into a majority of patients, will not cause an undesirably adverse, long-lived or escalating biological reaction or response. Such a response is distinguished from a mild, transient inflammation which typically accompanies surgery or implantation of foreign objects into a living organism.

The term "distal," as used herein, refers to a direction that is generally towards a target site within a patient's anatomy during a medical procedure.

The term "proximal," as used herein, refers to a direction that is generally towards a physician during a medical procedure.

The term "stricture," as used herein, refers to any narrowing of a bodily lumen in relation to an adjacent lumen portion.

DETAILED DESCRIPTION

Figure 1A:
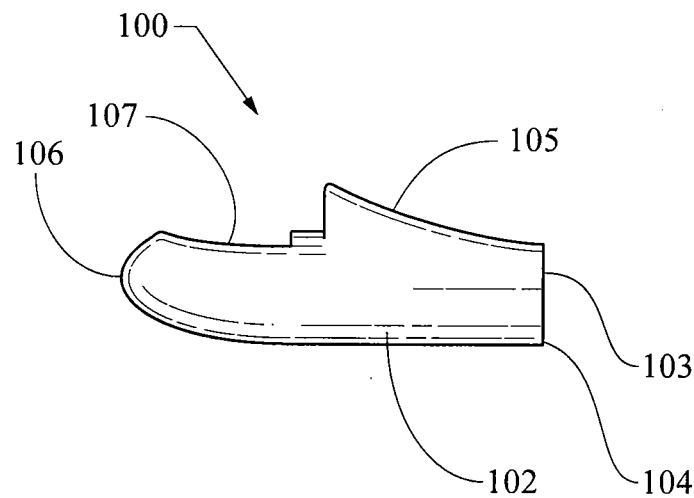
FIGS. 1A-1D depict endoscope cap 100 with a stationary ramp 105.
Figure 1B:
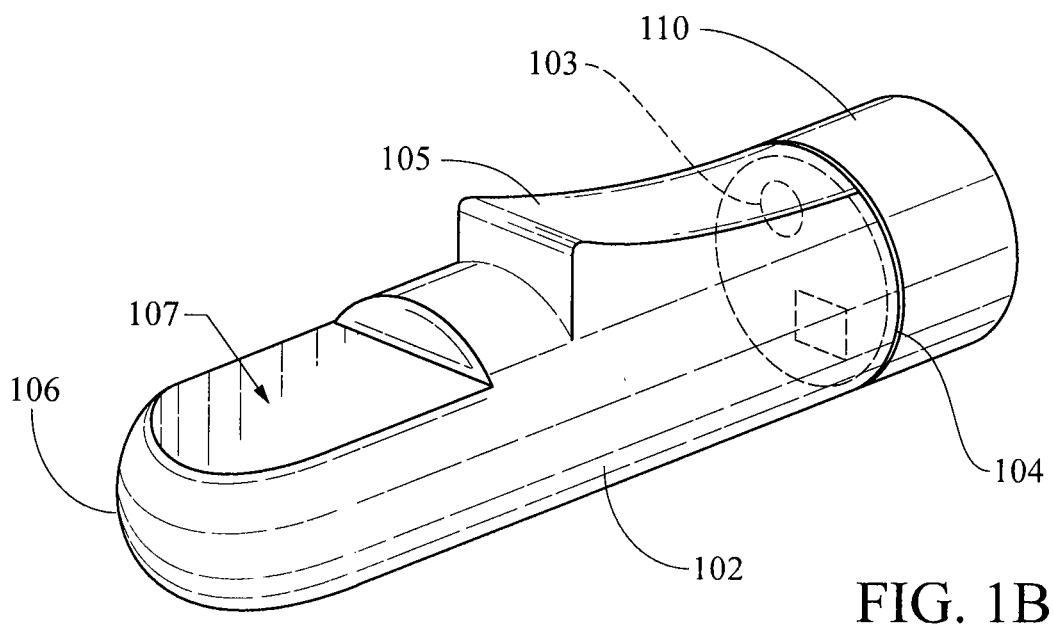

FIGS. 1A-1B depict an endoscope cap 100. The cap includes a body 102 having a proximal end 104 and a distal end 106. The proximal end 104 includes an aperture 103 configured to receive a distal portion of an endoscope. Cap 100 further includes a ramp 105 that can be used to deflect medical devices toward a selected target anatomy. Cap 100 further includes a side aperture 107 configured to accommodate the endoscope's visualization devices (e.g., camera, CCD, or fiber-optic element) and working channel(s).

Body 102 may be constructed of rigid material(s). In some embodiments, all or a portion of the body may be generally transparent. For example, the body may be constructed of a clear polycarbonate polymer. Alternatively, it may be constructed of another clear, translucent, or opaque polymer such as polyurethane, acrylic, or nylon. Body 102 preferably is dimensioned such that its outer diameter is about the same as the outer diameter of the endoscope on which cap 100 is to be used. For example, body 102 may have an outer diameter of about 8.5 mm to about 12 mm for use with endoscopes having those outer diameters. The skilled artisan will appreciate that body 102 may be dimensioned appropriately for use with endoscopes having greater or lesser diameters, and it may also have a cross-section configured for use with a similarly-shaped endoscope.

In some embodiments, the cap may include an engagement portion 110 configured to secure the cap to the endoscope. The engagement portion may be integral with or attached to proximal end 104 of the cap. The engagement portion, which preferably extends proximally from body 102 may be constructed from a flexible material that provides a frictional inner diameter surface. For example, the engagement portion may be constructed of a clear polyurethane that is molded to body 102. In other embodiments, it may be constructed from, for example, silicone or another soft polymer that will provide an ability to mount and frictionally (but removably) attach cap 100 to the endoscope.

Figure 1C:
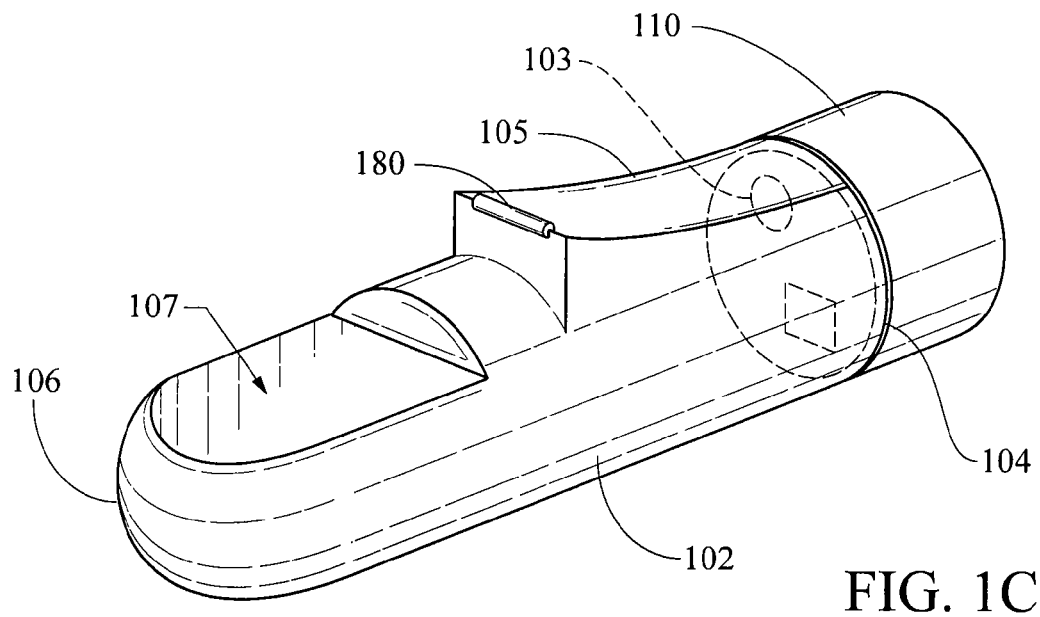
Figure 1D:
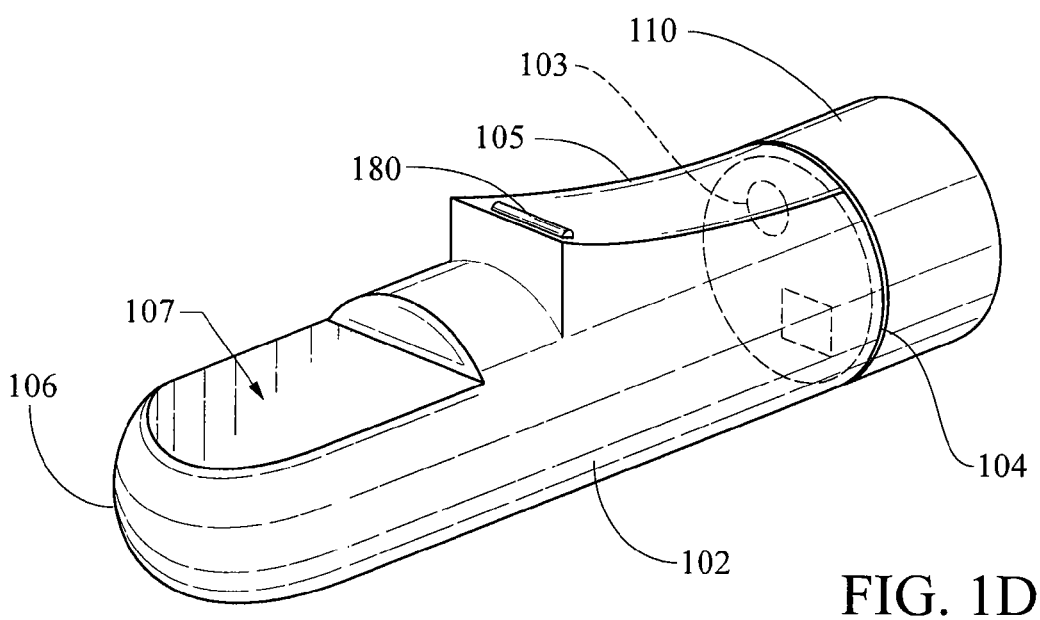

Optionally, cap 100 may include a roller attached to body 102 to facilitate advancement of the tether and other devices thereover. For example, FIGS. 1C-1D depict ramp 105 having a roller 180 recessed within the ramp surface near the top of the ramp. The roller may be supported by pins or the like; the pins may be attached to or partially embedded in the material of the cap. Alternatively, the ramp can be fabricated such that the roller can be snapped into position within the recess. The roller may contribute to a reduction in friction as the tether and other devices are advanced over the ramp. The roller may be fabricated to any appropriate dimensions for the intended use. For example, the roller may have a length about three-fourths that of the width of the ramp, such as depicted in FIGS. 1C-1D.

The cap may include any suitable structure or materials configured to attach the cap to the endoscope. For example, the cap may include an adhesive, magnets, a threaded surface, a detent structure, or other structures and materials known in the art. In another alternative embodiment, the endoscope may include a structure near its distal end for engaging the cap, such as for example, complementary threaded surfaces, interlocking tabs/slots, or another structure configured to attach the cap to the endoscope. Illustrative examples of such engagement portions can be found in U.S. Patent Application Publication No. 2009/0105539, the disclosure of which is herein incorporated by reference in its entirety.

Figure 2A:
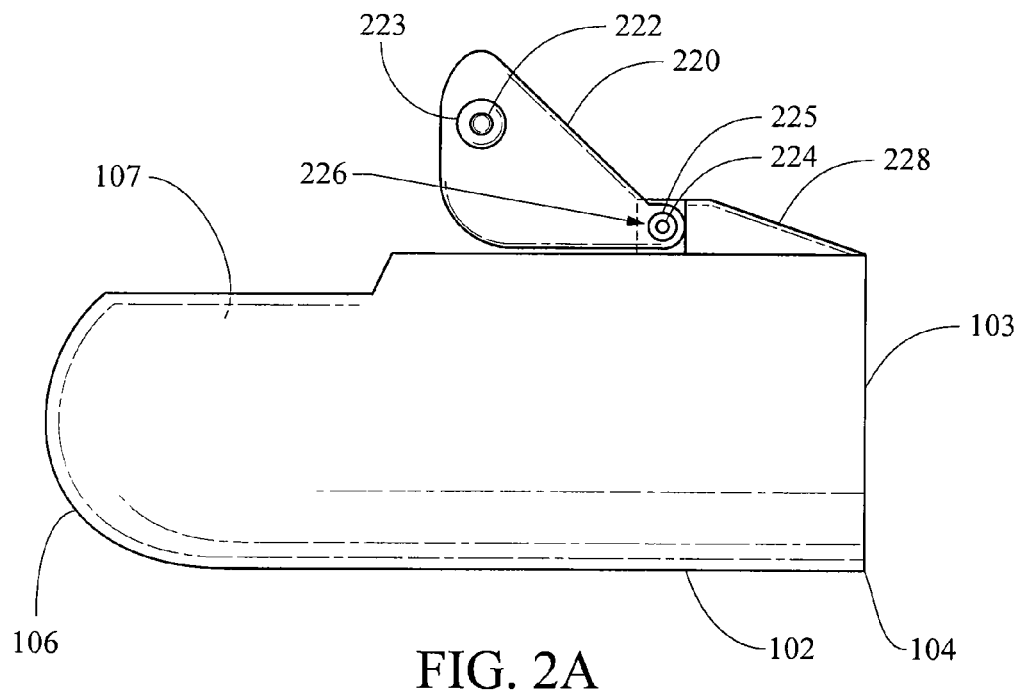
Figure 2B:
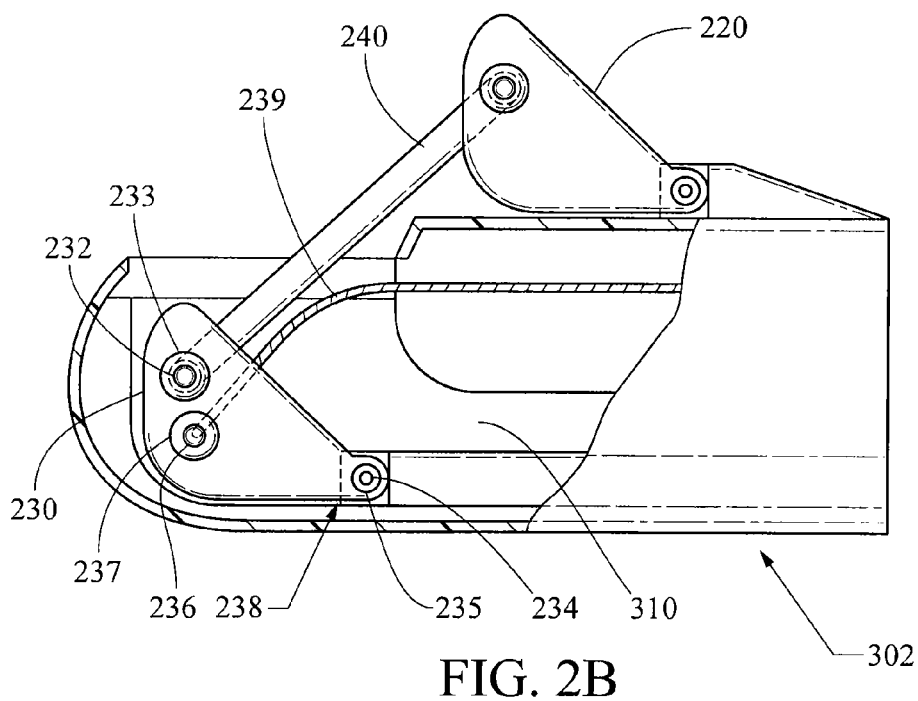

FIGS. 2A-2C show another embodiment of cap 100 including a ramp 220 pivotally attached to body 102. The ramp includes transverse passageways 222 and 224. Optionally, each respective passageway may include metal sleeves 223 and 225. Ramp 220 is pivotally attached to the cap by a ramp turning support 226, part of which is partially disposed through transverse passageway 224. The cap may further include a stationary ramp 228 configured to provide smooth transition from the external surface of the endoscope to ramp 220.

FIGS. 2B-2C depict the cap of FIG. 2A disposed on the distal end of an endoscope 302. The endoscope includes an elevator 230 that may be detachedly connected to ramp 220 by a connecting member 240. Elevator 230 includes transverse passageways 232, 234, and 236. Optionally, each respective passageway may include metal sleeves 233, 235 and 237. The elevator is pivotally attached to the endoscope by an elevator turning support 238, part of which is partially disposed through transverse passageway 234. An elevator wire 239 is connected at one end to elevator 230, and operatively connected at the other end to a control system located at the proximal portion of endoscope 302. Manipulation of the control system moves the elevator wire relative to the endoscope. As the elevator wire is retracted toward the proximal portion of the endoscope, elevator 230 moves about the elevator turning support 238. The elevator may be used to deflect devices delivered through the endoscope. For example, the elevator may be used to deflect a wire guide into the biliary system of a patient. A more detailed description of a similar endoscopic elevator apparatus can be found in U.S. Patent Application Publication No. 2007/0208219, the disclosure of which is herein incorporated by reference in its entirety.

The connecting member 240 includes an elongate portion 242 and two attachment elements 244, each attachment element disposed at an end of the elongate portion (FIG. 2D). The connecting member may be attached to elevator 230 and ramp 220 by inserting the attachment elements into transverse passageways 222 and 232. Attachment elements 244 may be cylindrically shaped structures attached to or integral with elongate portion 242. Preferably, the attachment elements can engage in axial motion about their respective central axes. For example, the attachment elements may include an outer portion and an inner portion separated by bearings that allow the outer portion to rotate about the attachment element central axis. The attachment elements may include any suitable structural elements necessary to engage the elevator 230 and ramp 220. For example, attachment elements 244 and transverse passageways 222 and 232 may have complimentary threaded surfaces.

When elevator 230 and ramp 220 are attached by connecting member 240, actuation of elevator 230 causes actuation of ramp 220. FIG. 2B shows elevator 230 and ramp 220 in a first configuration wherein elevator wire 239 is not retracted toward the proximal portion of the endoscope. FIG. 2C shows elevator 230 and ramp 220 in a second configuration wherein the elevator wire is retracted toward the proximal portion of the endoscope. As a medical device is advanced down alongside the endoscope, ramp 220 may be actuated from the first configuration to the second configuration to deflect the device toward the selected target anatomy. The skilled artisan will appreciate that in some cases, ramp 220 need not be fully actuated from the first configuration to the second configuration, but rather may be actuated to a configuration as needed for the particular procedure.

The presently disclosed ramps may be comprised of any suitable biocompatible material(s). In some embodiments, the ramps may be comprised of the same material as body 102. In other embodiments, the ramps may be comprised of a different material from body 102 or a combination thereof. Preferably, the ramps are comprised of a polymeric material. Properties of the ramp, such as flexibility/rigidity, may be adjusted by selection of an appropriate polymer as is known in the art. For example, polymers with a low coefficient of friction may be particularly suitable for various embodiments, while polymers with a high coefficient of friction may be suitable in other embodiments, such as for ramps configured to grasp a delivered device. Suitable polymeric materials include, but are not limited to, polytetrafluoroethylene, polyethylene, ultra-high molecular weight polyethylene, polypropylene, perfluoroelastomer, fluoroelastomer, nitrile, neoprene, polyurethane, silicone, styrene-butadiene, rubber, polycarbonate, acrylic, nylon, or combinations thereof.

The ramps may be configured to a variety of angles of elevation relative to the body 102. In general, however, the ramps present an angle of elevation ranging from about 1 degree to about 90 degrees relative to body 102, preferably about 5 degrees to about 75 degrees, more preferably about 10 degrees to about 60 degrees, and most preferably about 20 degrees to about 45 degrees. The ramp incline surface may be a uniform planar surface, or alternatively, may be a curvilinear surface. Preferably, the ramp surface is atraumatically shaped. For example, ramp 220 as shown in FIG. 2A presents an atraumatic profile with rounded edges along the ramp surfaces.

In some embodiments, the ramps may comprise surface structures configured to receive a delivered device. For example, ramps 105 and 220 may comprise a grasping slot configured to grasp another device. The grasping slot may take on any suitable shape or form for grasping the device. Suitable grasping configurations are disclosed in U.S. Patent Application Publication No. 2007/0208219, and may be applied to the presently disclosed ramps.

FIG. 3 depicts a device 320 that may be delivered to a selected target anatomy. Device 320 is intended to be a generic representation of any device that may be deflected by the presently disclosed endoscope cap. Device 320 may be a device adapted to provide therapy or diagnosis to the selected target anatomy, or alternatively, a device configured to deliver another therapeutic or diagnostic device to the selected target anatomy. Device 320 may be, for example, a nasoenteric tube, a J portion of a PEG-J tube, a colon decompression tube, a biliary stent, a delivery catheter, an overtube, an introducer sheath, or another device. Device 320 includes a proximal end 324 and a distal end 326. In some embodiments, as will be explained in greater detail below, device 320 may have a coupling element 322 complimentary to and configured to couple with another coupling element. In other embodiments, coupling element 322 may be absent from device 320.

Figure 4:
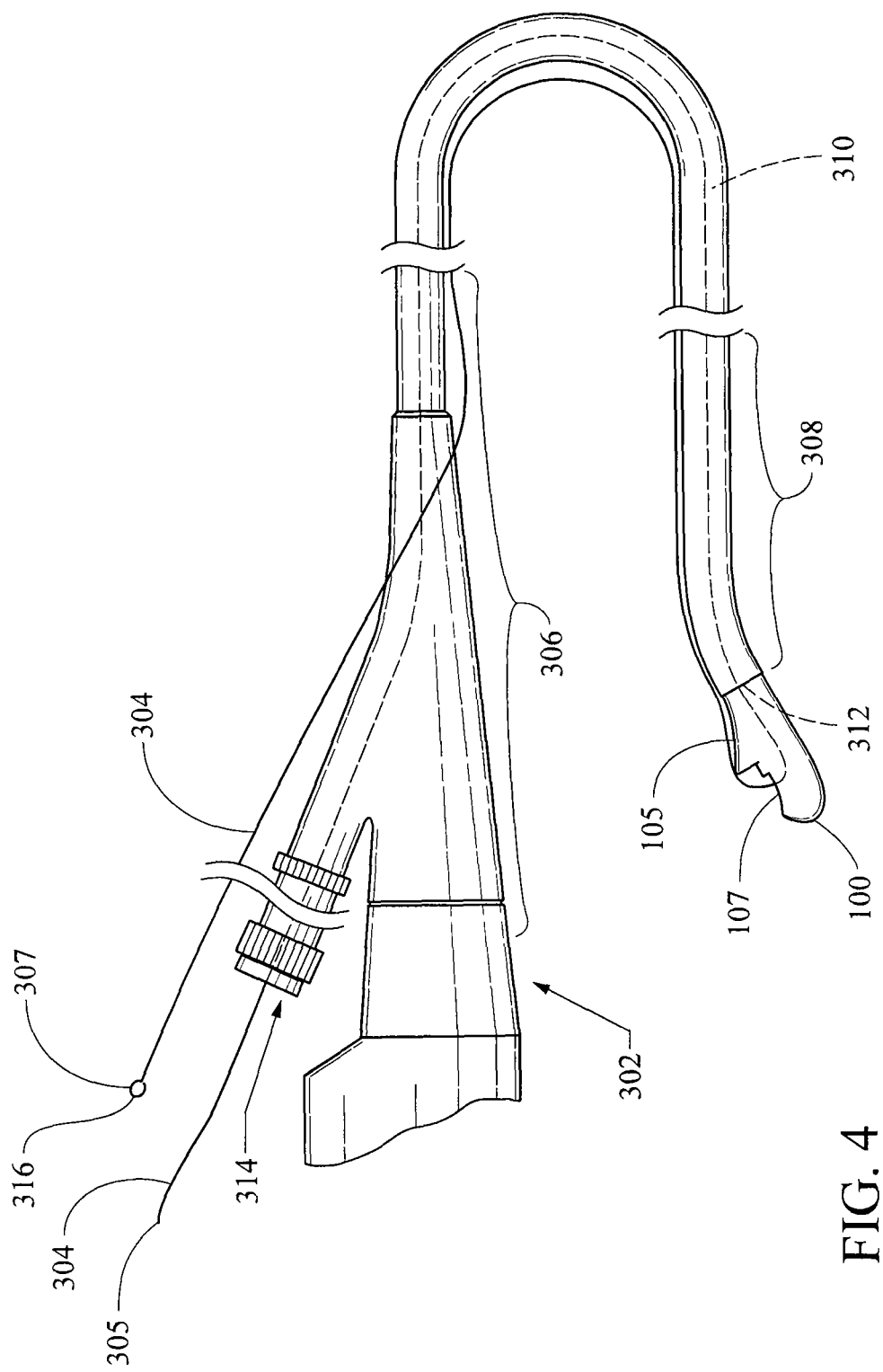
FIG. 4 depicts cap 100 and a tether system.

FIG. 4 shows cap 100 disposed on the distal end of endoscope 302 wherein the endoscope includes a tether system. The tether system may be used to pull devices down alongside the endoscope from a proximal portion 306 to a distal portion 308. Endoscope 302 has a working channel 310 extending from the proximal portion to the distal portion. The working channel connects to an aperture 312 disposed at the distal portion. Aperture 312 is aligned with aperture 107 of cap 100. Tether 304 extends externally alongside the endoscope from the proximal portion 306 to the distal portion 308 and enters working channel 310 via apertures 107 and 312. The tether extends back through the working channel to proximal portion 306 and exits at port 314. The tether includes a first end 305 and a second end 307. The tether may include a coupling element 316, preferably located at second end 307. The coupling element may be attached to or integrally formed with tether 304. The coupling element may be attached to the tether by glue, adhesive, or suture, for example. Once endoscope 302 has reached a selected target anatomy and device 320 has been coupled to the tether, the device may be advanced to the distal portion of the endoscope by pulling the tether back through working channel 310 from port 314. Preferably, device 320 can be pushed from its proximal end 324 while the tether is used to pull from its distal end 326.

Tether 304 may be a strap, a wire, a suture, a thread, or any other device capable of functioning as a tether suitable for the intended use. Preferably, the tether is configured to bend without kinking. In cases where additional instruments will be introduced through the endoscope working channel or where the working channel will be used to provide aspiration or decompression, preferably the tether occupies minimal space therein and does not substantially interfere with the procedure. In one embodiment, the tether may be a wire having a 0.035 millimeter diameter, and can be used with an endoscope having a lumen diameter of 4.8 millimeters, for example. In another embodiment, the tether may be a flexible strap, such as a nylon strap, configured to conform to an inner surface of the endoscope working channel. The tether may be fabricated from a variety of biocompatible materials, including metal alloys and polymeric materials. Suitable polymeric materials include, for example, nylon, polyester, polyethylene, ultra-high molecular weight polyethylene, or polypropylene. Suitable metal alloys include, for example, nickel-titanium alloys. The tether can be coated with one or more materials. Preferably, at least a portion of the tether is coated with a hydrophilic or other lubricious material that can facilitate advancement of the tether through the anatomy of the patient. The tether may be coated with, for example, SLIP-COAT® Biopolymer, STS Biopolymers, Inc., Henrietta N.Y.

The coupling elements 316 and 322 may include any suitable structures configured to temporarily couple two medical devices. For example, the coupling elements may include a closed loop structure as depicted in FIGS. 3 and 4. The coupling elements may include releasable or breakable sutures, temporary or dissolvable bonds or adhesives, magnets, or a combination thereof. The coupling elements may include a biocompatible ball which is crimped, glued, or otherwise designed to slide off or break apart with the application of sufficient amount of pull force (e.g., 3 pounds), and can thereafter be safely passed through the gastrointestinal system or be absorbed thereby. Optionally, device 320 may be coupled directly to the tether, with for example, breakable or dissolvable sutures.

The tether system may further include a guiding device used to advance devices beyond the distal portion of the endoscope (FIGS. 5A-5E). Guiding device 400 includes a flexible or semi-flexible elongate member 402, a fulcrum 404, and a variable stiffness cable 406. The elongate member 402 includes a distal portion 410 and a proximal portion 412. The elongate member may have a range of lengths and diameters depending on the size of the working channel of the endoscope to be used and the procedure to be performed. In general, the length of elongate member 402 ranges from about 100 cm to about 300 cm. The cross-sectional diameter generally ranges from about 1 mm to about 3 mm, and is preferably configured for advancement through the working channel of the endoscope. The skilled artisan will appreciate that all dimensions provided herein are intended as examples only, and guiding devices having different dimensions may be substituted for a particular use.

Elongate member 402 includes a biocompatible material that encases variable stiffness cable 406, shielding it from direct exposure to the patient anatomy. The material may be, for example, expanded polytetrafluoroethylene, polytetrafluoroethylene, polyethylene, or polyurethane. In one exemplary embodiment, elongate member 402 may be fabricated by placing heat shrink tubing, such as heat shrink polytetrafluoroethylene tubing, over the variable stiffness cable 406 and thereafter heat shrinking the tubing in place. The elongate shaft may comprise one or more materials providing the shaft with properties of sufficient strength, flexibility, and resistance to compression in order to traverse tortuous areas of the anatomy. Such materials include nylon, polyether block amides, polyethylene terephthalate, polytetrafluoroethylene, polyetheretherketone, or combinations thereof. The skilled artisan will appreciate, however, that the elongate member may be constructed from other biocompatible materials as is known in the art to provide the desired properties.

Figure 5A:
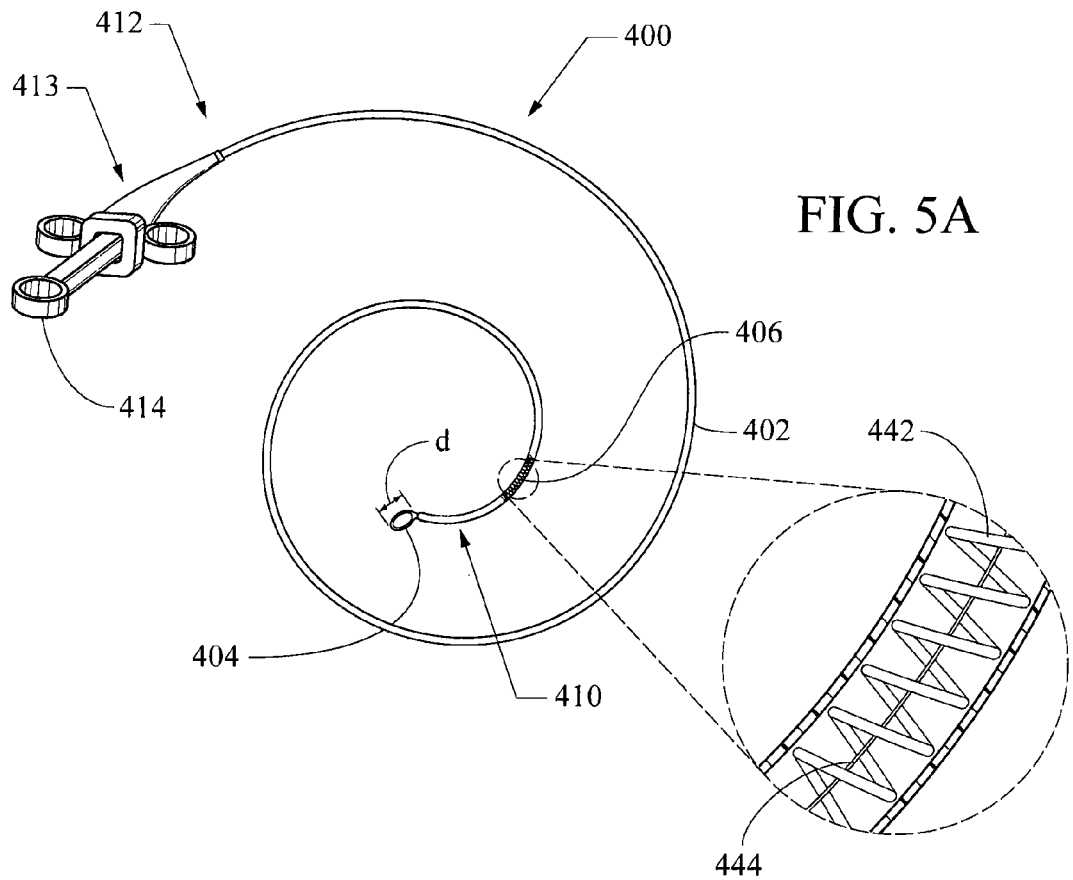
FIGS. 5A-5C depict guiding device 400.
Figure 5B:
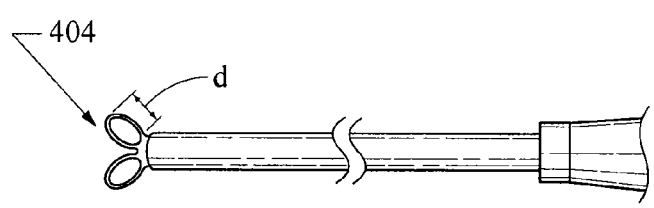
Figure 5C:
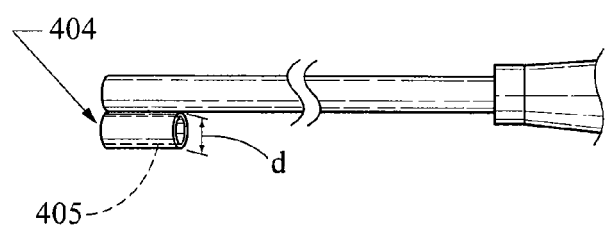

Fulcrum 404 is attached to or integrally formed with distal portion 410 of elongate member 402. The fulcrum may be any suitable structure configured to receive tether 304 and provide a point at which the tether can be advanced through or around. Fulcrum 404 may be, for example, a single loop structure (FIG. 5A), a double loop structure (FIG. 5B), or a cylindrical structure having a lumen 405 extending therethrough (FIG. 5C). The fulcrum has a diameter d preferably ranging from about 1 mm to about 3 mm. In some embodiments, the fulcrum may be constructed of wire, suture, or thread. In other embodiments, the fulcrum may be constructed of a more rigid material. In general, however, fulcrum 404 may comprise any material suitable for the intended use. The fulcrum may include, for example, polymeric materials such as nylon, and/or metallic materials such as nickel-titanium alloys.

Portions of the guiding device can be coated with one or more materials. Preferably, at least a portion of elongate member 402 is coated with a hydrophilic or other lubricious material. Hydrophilic or other lubricious coatings are known to facilitate advancement of devices through patient anatomy or introducer devices. In some embodiments, fulcrum 404 may be comprised of and/or coated with a material that facilitates smooth advancement of the tether therethrough. Preferred materials include polytetrafluoroethylene, ultra-high molecular weight polyethylene (UHMWPE), nylon, and polyoxymethylene.

Variable stiffness cable 406 is disposed through elongate member 402 and includes a helical spring 442 extending from proximal portion 412 to distal portion 410 near fulcrum 404. The spring includes a small pitch between the adjacent turns. A wire 444, such as a stainless steel wire, extends through the central bore of spring 442 and is affixed to the distal end thereof. Alternatively, the wire and the spring may both be affixed to a distal tip. Wire 444 is operatively connected to a hand assembly 413 located proximal to proximal portion 412. Hand assembly 413 includes an actuator 414 that can be used to compress or decompress spring 442. For example, in some embodiments, retraction of the actuator in the proximal direction retracts wire 444. This retraction of the wire reduces the distance between the turns in spring 442, and thereby reduces the spring's flexibility. Additional examples of variable stiffness cables are disclosed in U.S. Pat. Nos. 4,215,703 and 3,854,473, the disclosures of which are herein incorporated by reference in their entirety.

Figure 5D:
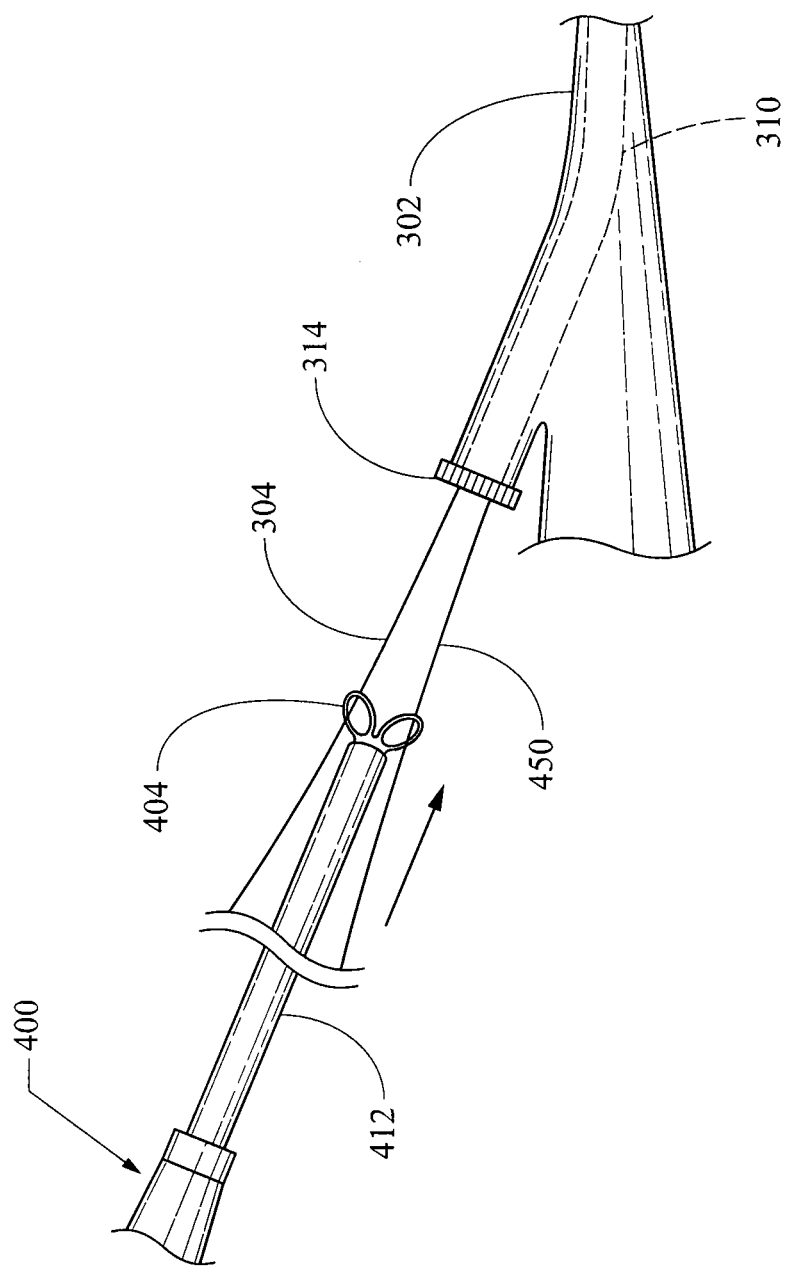
FIG. 5D depicts loading of guiding device 400 onto a tether and a wire guide.

Guiding device 400 may be loaded onto tether 304 at the proximal portion of the endoscope by passing first end 305 of tether 304 through fulcrum 404. Preferably, the guiding device is also loaded onto the proximal end of a wire guide 450 that exits port 314 and has been used to cannulate the target anatomy. The tether and the wire guide may be passed, for example, through the double loop fulcrum 404, as depicted in FIG. 5D. The elongate member 402 can then be advanced into the working channel 310 via port 314. Thereafter, the elongate member may be advanced through the working channel, out apertures 107 and 312, and to a selected target anatomy beyond distal portion 308. In some embodiments, an endoscopic elevator apparatus, such as elevator 230, may be used to aid in advancement of elongate member 402 into the selected target area. As the elongate member advances beyond the distal portion of the endoscope, preferably the tether becomes looped around the fulcrum and is pulled into the target anatomy.

Figure 5E:
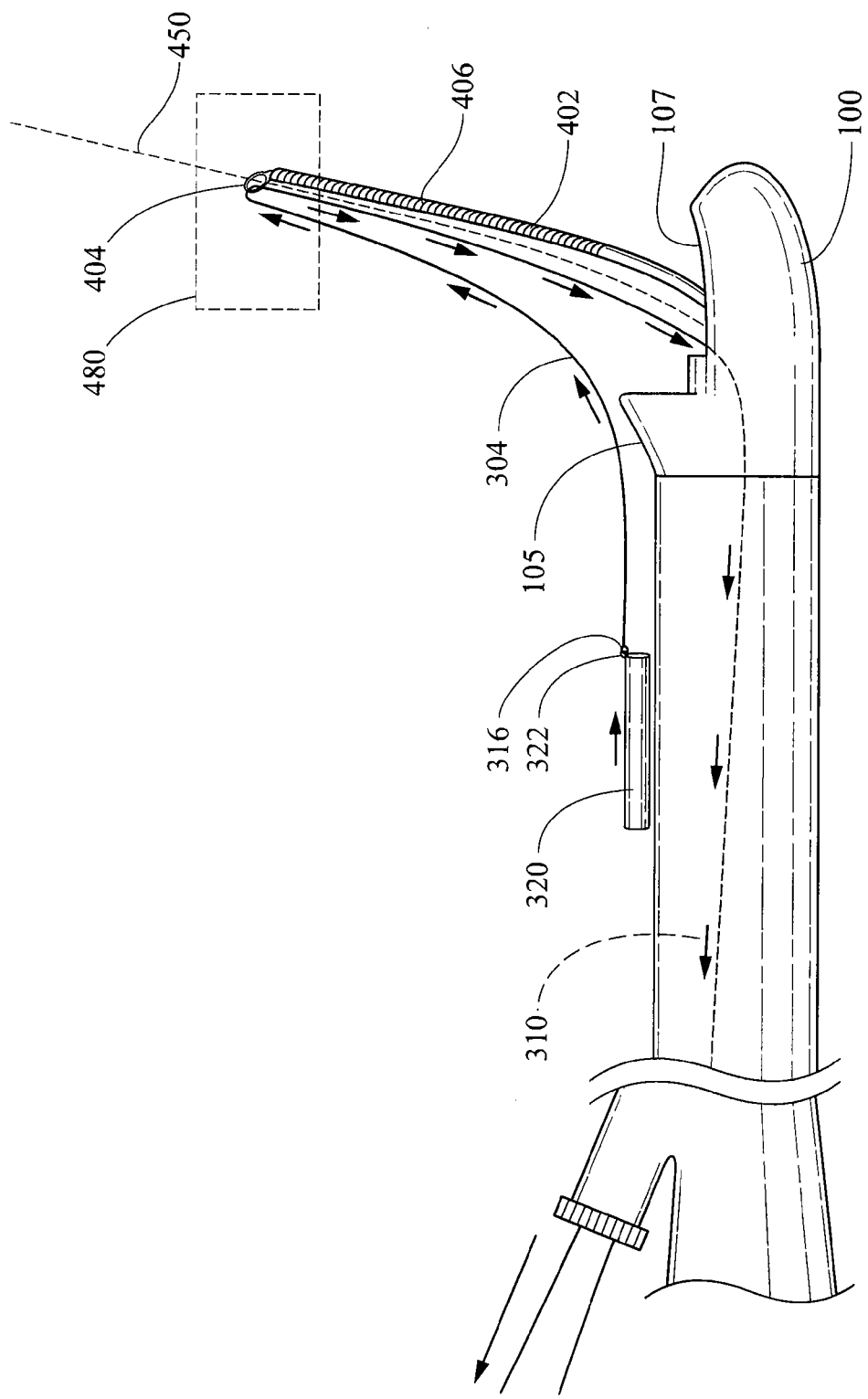
FIG. 5E depicts endoscope cap 100 and guiding device 400.

Once distal portion 410 of elongate member 402 reaches a target anatomy 480, the variable stiffness cable 406 may be used to stiffen and anchor the elongate member in place (FIG. 5E). The tether can then be pulled back through working channel 310 from port 314, thereby advancing a coupled device 320 toward distal portion 308 of the endoscope. Upon reaching the distal portion of the endoscope, device 320 may advanced onto ramp 105. With continuous pulling via the tether, and optional pushing from the proximal end, device 320 may be deflected by ramp 105 and continue to advance along the guiding device toward the target anatomy.

During introduction of the endoscope and extension of the guiding device into the target anatomy, the tether can be held secure as needed. Preferably, the tether is long enough so that control can be maintained at both ends while the endoscope and guiding device are advanced to the target anatomy. In other words, preferably the tether is greater than two times the length of the endoscope. In embodiments using the guiding device, preferably the tether is greater than two times the additive length of the endoscope and the length of the portion of elongate member 402 that extends out of aperture 312 and to the target anatomy. The portion of tether exiting port 314 can be held secure at the port by, for example, a locking device (e.g., Fusion® Wire Guide Locking Device, Cook Endoscopy Inc., Winston-Salem, N.C.), or by holding the tether. Likewise, the other end of the tether, specifically the portion of tether running external along the endoscope to the proximal portion 306, can be held secure by a locking mechanism or similar device, or by holding the tether. As elongate member 402 or device 320 is advanced into the target anatomy, the tether can be unlocked as needed.

Figure 6:
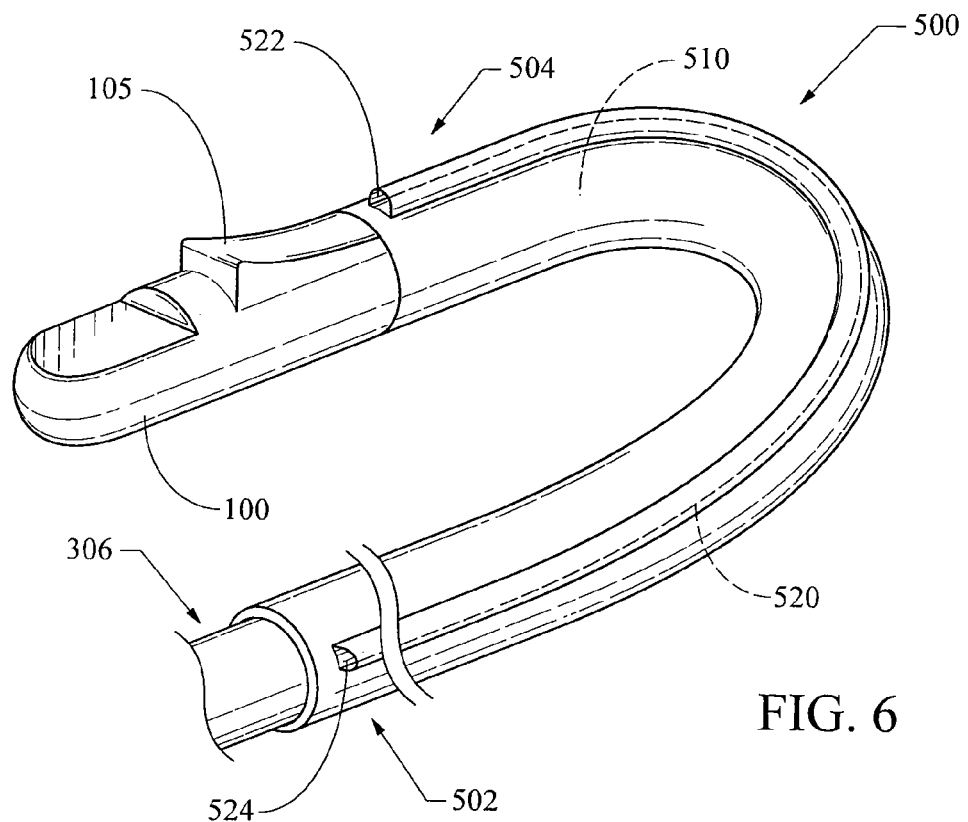
FIG. 6 depicts endoscope cap 100 and sheath 500.
Figure 7:
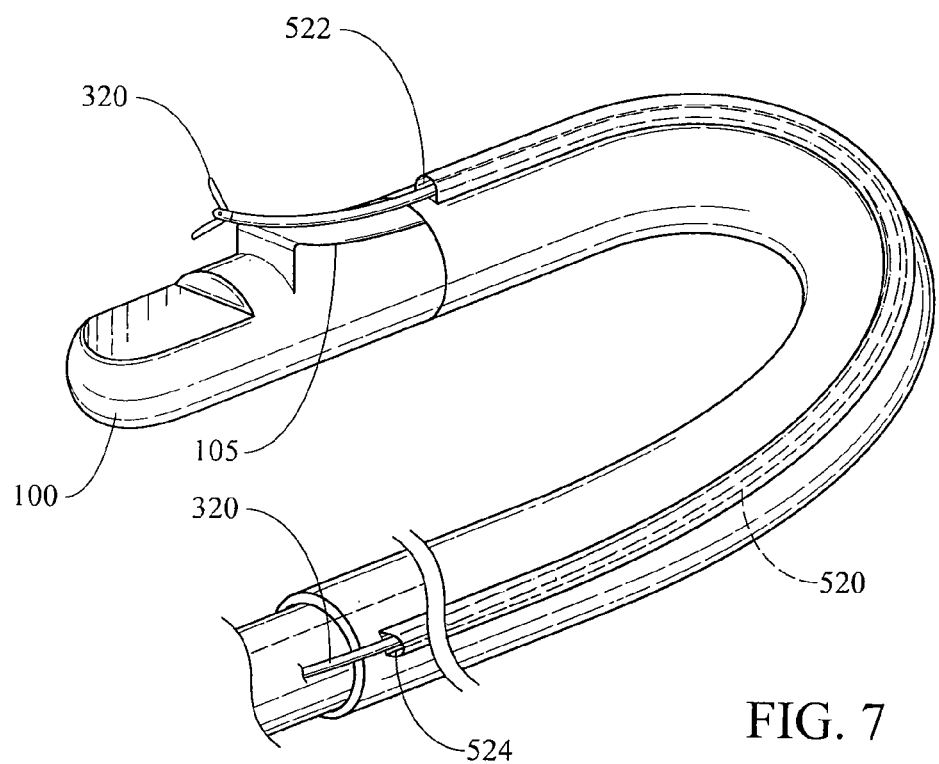
FIG. 7 depicts endoscope cap 100 and sheath 500.

FIG. 6 shows cap 100 disposed on the distal end of an endoscope wherein the endoscope includes a sheath 500. Sheath 500 includes a proximal portion 502 and a distal portion 504. The sheath includes a first lumen 510 for an endoscope and a second lumen 520 for devices delivered alongside the endoscope. Lumen 520 extends from the proximal portion 502 to the distal portion 504 and has distally located aperture 522, and proximally located aperture 524. Device 320 may be advanced down lumen 520 and thereafter deflected toward a selected target anatomy. In one embodiment, the device may be pushed down the sheath lumen, optionally with the aid of a pushing catheter or other similar device. FIG. 7 shows a grasping device 320 that has been pushed down lumen 520 and thereafter deflected by ramp 105. In other embodiments, the device may advanced down lumen 520 with the tether system as described, wherein a portion of the tether is disposed through the length of lumen 520 to begin the procedure. In other embodiments, the device may be advanced down lumen 520 by pushing from the device proximal end 324 while pulling at the device distal end 326. As depicted, endoscope 302 is disposed through lumen 510, the sheath extending over the endoscope proximal portion 306 to distal portion 308. The sheath may have a range of widths and lengths depending on the size of the endoscope to be used. In general, the sheath length ranges from about 100 cm to about 200 cm; and the sheath has a wall thickness of between about 0.1 mm to about 8 mm. In one embodiment, the sheath may be constructed from expanded polytetrafluoroethylene (ePTFE). The sheath and the cap may be integrally attached at the distal end of the sheath and at the proximal end 104 of the cap. Alternatively, the cap may be configured to fit over the distal end of the sheath. For example, the cap can include, as described above, structures configured to frictionally engage the exterior of the endoscope and/or the exterior surface of the sheath.

Figure 8:
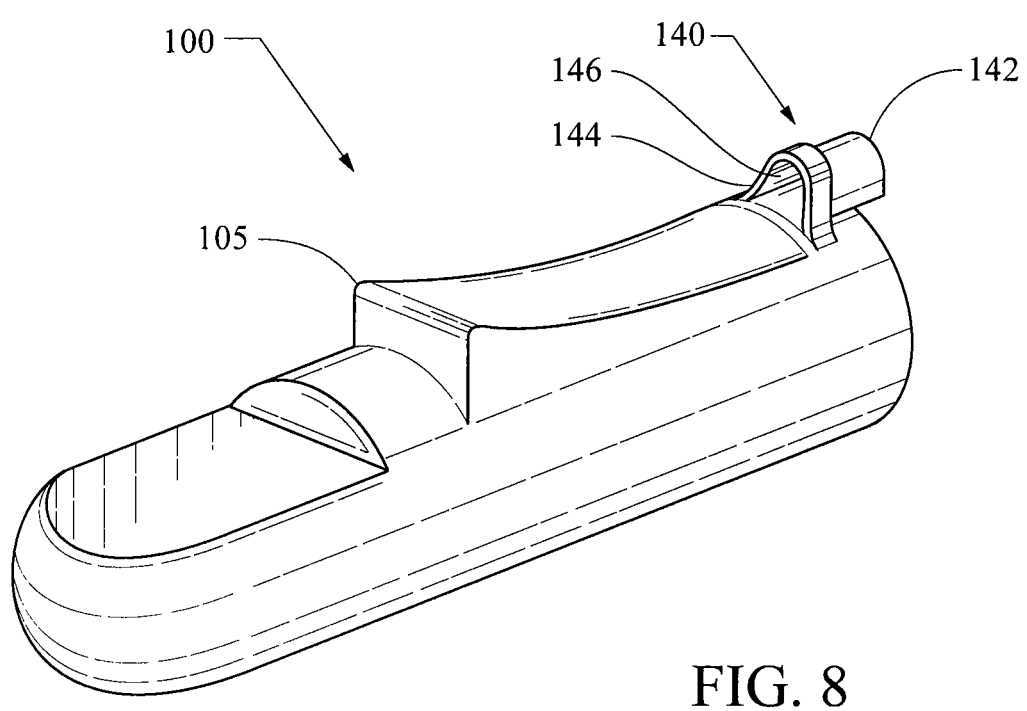
FIG. 8 depicts endoscope cap 100 including coupling member 140.

FIG. 8 depicts cap 100 including a coupling member 140 configured to engage lumen 520 at aperture 522 of sheath 500. Coupling member 140 includes a proximal portion 142 and a distal portion 144. The coupling member further includes a lumen 146 that extends through the proximal portion 142 to the distal portion 144 and is open at both ends. Lumen 146 is aligned with ramp 105 such that once device 320 exits the sheath lumen and lumen 146, the device will intersect ramp 105 and be deflected thereby. The proximal portion 142 is configured to slide into sheath lumen 520 at aperture 522 and frictionally engage the inner surface of lumen 520, thereby securing the coupling member to the lumen.

FIGS. 9A-9F demonstrate a method by which a medical device can be introduced alongside the endoscope to a selected target anatomy. In one exemplary embodiment, the endoscope cap can be used with Endoscopic Retrograde Cholangiopancreatography (ERCP). ERCP involves inserting a duodenoscope into a patient's mouth and through the esophagus, stomach, and duodenum until it reaches the area where the ducts of the biliary tree and the pancreas open into the duodenum. Devices delivered through the endoscope's working channel may then traverse the Papilla of Vater for access to the ductal system. Therein, these devices can be used to perform diagnostic and therapeutic procedures. Examples of such devices include wire guides, baskets, snares, stents, extraction balloons, introducer brushes, catheters, and baby endoscopes usually of 0.8 mm to 4 mm in diameter.

One ERCP procedure includes delivery of a plastic biliary stent into an area of the bile or pancreatic duct where a stricture is blocking drainage of fluid. The blockage may be caused by a tumor in the bile or pancreatic duct. Typically, by the time symptoms appear in the patient, the tumor is at an advanced stage and is deemed inoperable. As a result, management of the cancer usually focuses on palliation of the symptoms. As an alternative to surgical bypass procedures for palliation, a stent may be delivered by ERCP and positioned through the obstructed area so as to maintain a pathway for fluid to flow across. However, the maximum diameter of a plastic biliary stent generally depends on the diameter of the endoscope's working channel. As a result, in some instances multiple stents must be placed within the stricture to allow for sufficient drainage. Using the presently disclosed endoscope cap, plastic biliary stents having diameters larger than the endoscope's working channel can be delivered to the bile or pancreatic ducts. These larger tubes may facilitate more efficient drainage of the duct and may be less prone to clogging compared to their smaller counterparts.

Figure 9A:
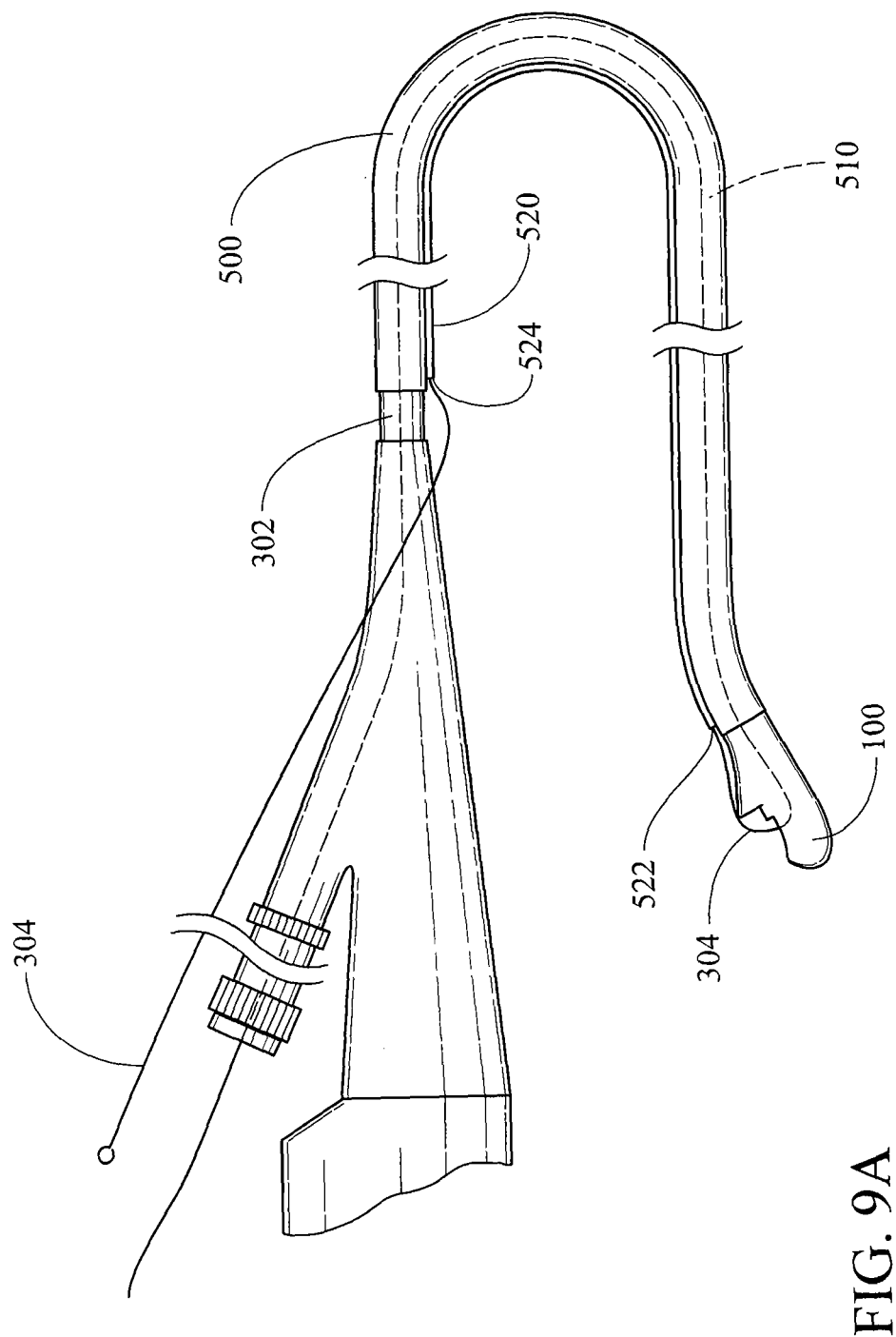
FIGS. 9A-9F depict delivery of a large plastic biliary stent into the common bile duct using endoscope cap 100.
Figure 9B:
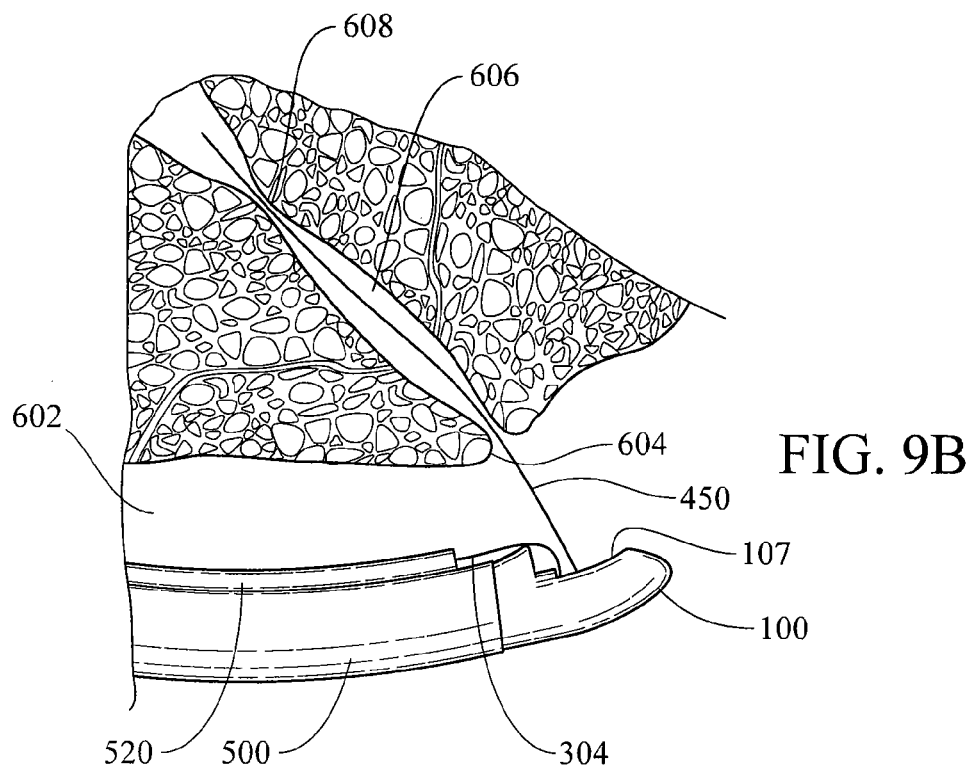
Figure 9C:
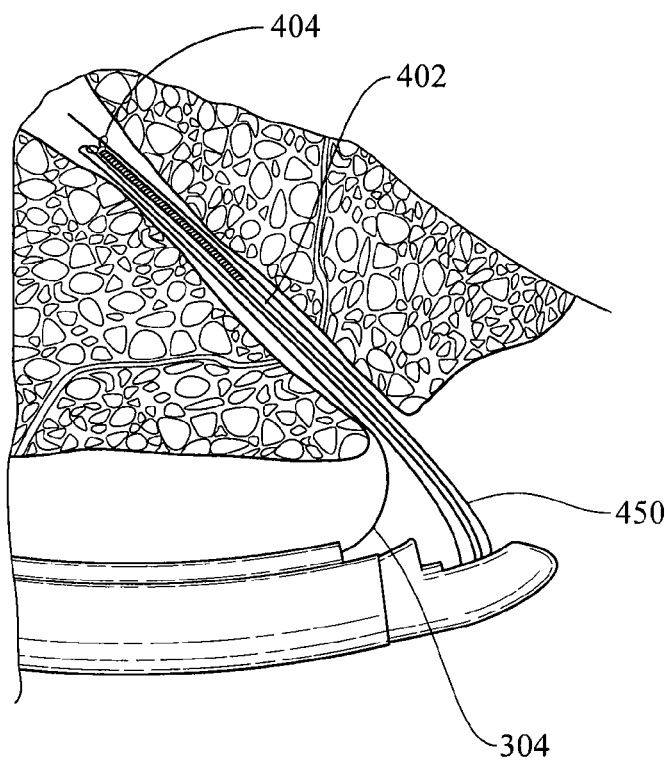

FIGS. 9A-9F illustrate delivery of a large plastic biliary stent 610 into the common bile duct using cap 100 including ramp 105. The tether 304, guiding device 400, and sheath 500 are also used to deliver the stent. The procedure begins with the tether disposed through lumen 520 and back through lumen 310, as depicted in FIG. 9A. The endoscope may then be advanced into the patient and positioned in the duodenum 602 to allow viewing of the Sphincter of Oddi and the Papilla of Vater 604, which lie at the opening to the common bile duct 606 and the pancreatic duct. Next, the wire guide 450 may be extended out of apertures 107 and 312, through the Ampulla of Vater and into the ductal system (FIG. 9B). Preferably, the wire guide is advanced past the stricture 608. A dilator catheter may be used as needed to facilitate cannulation of the duct. A more detailed description of cannulation of the common bile duct with the assistance of a dilator catheter is disclosed in U.S. Patent Application Publication No. 2005/0059890, the disclosure of which is herein incorporated by reference in its entirety. The guiding device 400 can be loaded over the wire guide and the tether 304 at the proximal portion of the endoscope. Elongate member 402 of the guiding device may be advanced through the endoscope's working channel and thereafter extended out of apertures 107 and 312 and into the ductal system, all the while advancing over the wire guide via fulcrum 404 (FIG. 9C). The endoscope may include an elevator apparatus, as described above, that may be used to deflect the guiding device toward the ductal system. As elongate member 402 advances into the ductal system, the tether will also be advanced by virtue of its contact with fulcrum 404. Preferably, fulcrum 404 is advanced past stricture 608 so that the biliary stent can be pulled into place when advanced into the target anatomy. Once elongate member 402 is advanced to the desired location, variable stiffness cable 406 may be engaged by manipulation of actuator 414, thereby causing stiffening of the elongate member 402. Stiffening anchors the elongate member in position and provides rigidity which can prevent buckling during delivery of device 320.

Figure 9D:
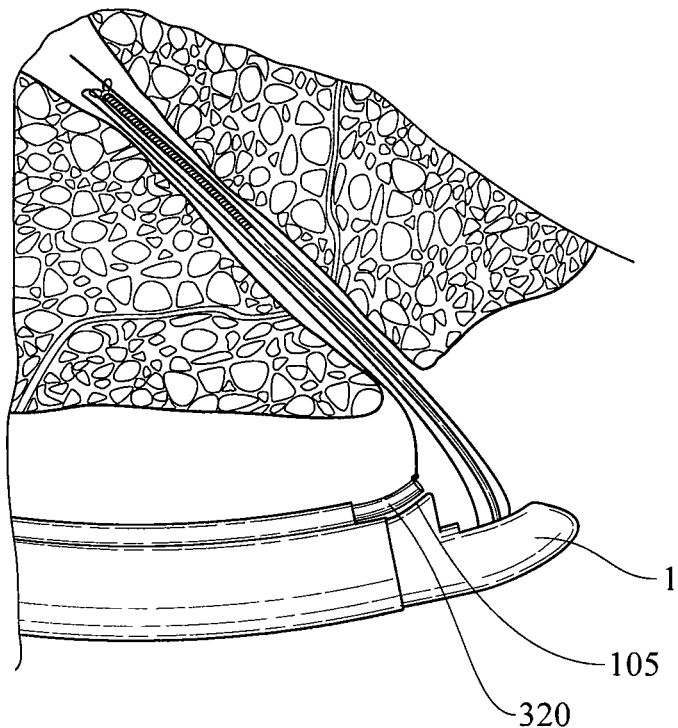

Next, the biliary stent may be coupled to the tether at the proximal portion of the endoscope. Preferably, the stent is loaded into and delivered via a delivery catheter that is configured to couple to the tether. The delivery catheter, as device 320, includes a coupling element 322 for coupling to the tether, and preferably includes a stiffening element or a partially rigid portion so that the catheter can be pushed from its proximal end 324. Pushing the stent or the delivery catheter can reduce tension on the tether during introduction and may reduce the incidence of mucosal trauma. Once coupled, device 320 may be advanced into lumen 520 at aperture 524. Device 320 may be advanced through lumen 520 and thereafter to the distal portion of the endoscope. Upon exiting lumen 520 at aperture 522, preferably device 320 is deflected by ramp 105 toward the Papilla of Vater 604 (FIG. 9D).

Figure 9E:
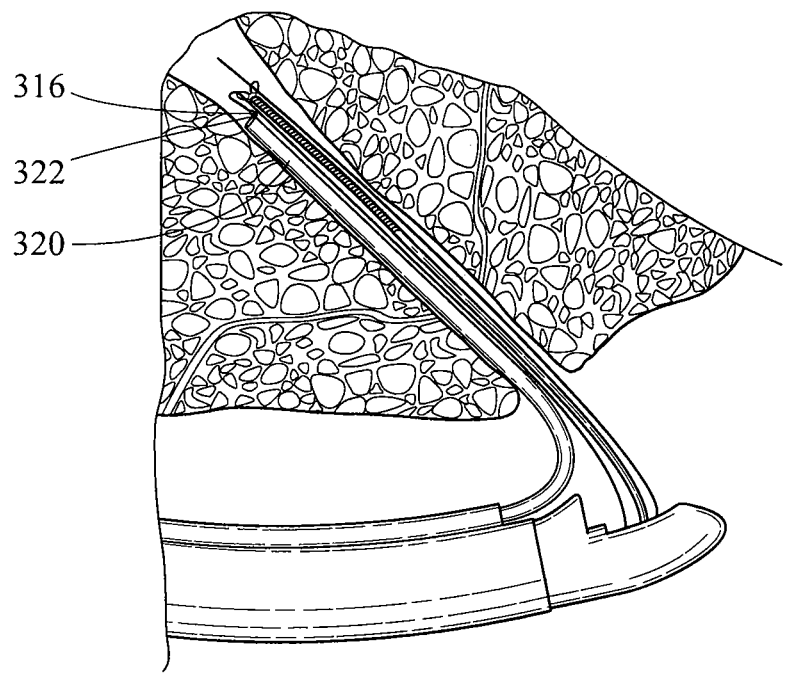
Figure 9F:
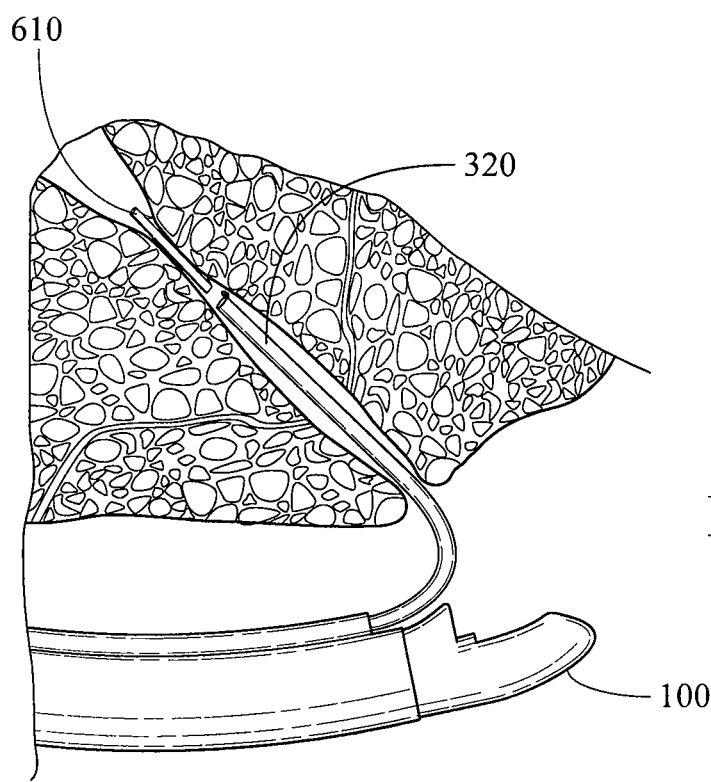

The delivery catheter may be advanced along elongate member 402 of guiding device 400 by continuing to push from the proximal end while pulling with tether 304. Preferably, the delivery catheter is advanced to distal portion 410, and thus, the target anatomy (FIG. 9E). Once the delivery catheter reaches the target site (i.e., the stricture), it may then be decoupled from the tether. For example, the delivery catheter may be held at the proximal end while the tether is pulled back at port 314 with sufficient force to detach coupling element 316 from coupling element 322, thereby decoupling the delivery catheter from the tether. The tether may then be pulled out of the ductal system and back into the endoscope working channel 310. The guiding member 400 and subsequently the wire guide 450 may be advanced out of the ductal system and back into the endoscope. Next, the biliary stent 610 may be delivered to the site of the stricture 608 by pushing the stent out of the delivery catheter using an internal pushing catheter (FIG. 9F). The delivery catheter may then be removed from the patient anatomy. The skilled artisan will appreciate that the steps of accessing, delivering, decoupling, and removal of devices from the target anatomy may be varied as necessary. For example, if additional procedures are to be performed using the wire guide, it may be preferable to only partially retract the wire guide from the bile duct.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

The invention claimed is:

1. An endoscope cap for use with an endoscope having a tubular shaft extending between a proximal end and a distal end, and a working channel extending through the tubular shaft and terminating at the distal end, the endoscope cap comprising:

a body comprising a cylindrical tubular portion extending between a proximal end and an enclosed distal end, the proximal end of the tubular portion having a diameter that is configured to be equal to a diameter of the distal end of the tubular shaft of the endoscope, the tubular portion comprising a first circumferential side and a second circumferential side opposite the first circumferential side;

a first aperture disposed at the proximal end and configured to receive the distal end of the endoscope therein such that the tubular portion of the body is aligned with the tubular shaft of the endoscope and extends distally beyond the distal end of the endoscope;

a stationary first ramp disposed between the proximal end and the distal end, and projecting outwardly from an outer circumference of the tubular portion of the body, wherein the first ramp is configured to project radially outwardly beyond an outer surface of the distal end of the endoscope, and is further configured to deflect an elongate medical device disposed externally to both the body and the endoscope in a first radial direction away from the endoscope; and a second aperture in communication with the first aperture and disposed on the tubular portion of the body between the first ramp and the distal end, wherein the second aperture is configured to deflect a second elongate medical device disposed through both the endoscope and the first aperture along a second radial direction away from the endoscope, wherein the second aperture and the ramp are both disposed on the first circumferential side of the tubular portion of the body.

2. The endoscope cap of claim 1 wherein the first ramp is integral with the body, the first ramp comprising a proximal end that is disposed adjacent to and extends distally from the proximal end of the body.

3. The endoscope cap of claim 1, further comprising an engagement portion proximal to the proximal end and configured to secure the endoscope cap to the endoscope.

4. The endoscope cap of claim 1 wherein the body comprises a polycarbonate, polyurethane, or nylon polymer.

5. The endoscope cap of claim 1 wherein the first ramp comprises polytetrafluorethylene, polyethylene, ultra-high molecular weight polyethylene, polypropylene, perfluoroelastomer, fluoroelastomer, nitirle, neoprene, polyurethane, silicone, styrene-butadiene, rubber, polycarbonate, acrylic, or nylon, or combinations thereof.

6. The endoscope cap of claim 1 wherein the first ramp comprises an angle of elevation relative to the body ranging from about 1 degree to about 90 degrees.

7. The endoscope cap of claim 1 wherein the first ramp comprises a grasping slot configured to receive a medical device.

8. The endoscope cap of claim 1 comprising a coupling member configured to couple with an endoscope sheath lumen disposed on an external surface of the endoscope, the endoscope sheath lumen configured for advancing devices along the external surface of the endoscope from a proximal portion of the endoscope to a distal portion of the endoscope.

9. The endoscope cap of claim 8 wherein the coupling member comprises:

a coupling member proximal portion and a coupling member distal portion; and a coupling member lumen extending from the coupling member proximal portion to the coupling member distal portion, the coupling member lumen open at both ends, wherein the coupling member proximal portion comprises an outer surface configured to frictionally engage an inner surface of the endoscope sheath lumen, and wherein the coupling member lumen is aligned with the first ramp.

10. The endoscope cap of claim 1 comprising a second ramp disposed distal to the first ramp.

11. The endoscope cap of claim 1 wherein the first ramp comprises a roller attached to an outer surface of the first ramp, the roller being configured to movably engage an elongate medical device disposed externally to both the body and the endoscope.

12. The endoscope cap of claim 1 wherein the first ramp comprises a concaved outer surface extending between a proximal end and a distal end of the first ramp, the proximal end of the ramp being disposed adjacent the proximal end of the body.

13. The endoscope cap of claim 1 wherein the cylindrical tubular portion of the body comprises a constant outer diameter along a majority of the length thereof, and wherein the first ramp projects outwardly from the constant outer diameter of the cylindrical tubular portion.

14. The endoscope cap of claim 1 wherein the first ramp comprises a continuous curvilinear surface extending between a proximal end and a distal end, the proximal end of the first ramp being disposed adjacent to the proximal end of the body, and the distal end of the first ramp being disposed adjacent to the second aperture.

15. The endoscope cap of claim 1 wherein the first ramp extends between a proximal end and a distal end, the distal end of the first ramp comprising a radially oriented surface extending outwardly from the tubular portion of the body.

16. An endoscopic system comprising:

an endoscope comprising a tubular shaft extending between a proximal end and a distal end, the distal end having a constant diameter, the endoscope further comprising a working channel extending through the tubular shaft and terminating at the distal end;

a first elongate medical device movably disposed alongside of and externally to the tubular shaft of the endoscope;

a second elongate medical device movably disposed through the working channel of the endoscope; and the endoscope cap of claim 1, wherein the first aperture is coupled to the distal end of the endoscope, wherein the tubular portion of the endoscope cap has a diameter that is equal to the diameter of the distal end of the endoscope, wherein the first ramp is engaged by the first elongate medical device, and wherein a second elongate medical device is simultaneously disposed through the first aperture and the second aperture.

17. An endoscopic system comprising:

an endoscope comprising a tubular shaft extending between a proximal end and a distal end, and further comprising a working channel extending through the tubular shaft and terminating at the distal end;

a flexible tether having a first portion and second portion, the first portion being movably disposed alongside of and external to the tubular shaft of the endoscope, the second portion being movably disposed through the working channel of the endoscope; and the endoscope cap of claim 1, wherein the first aperture is coupled to the distal end of the endoscope, and wherein the flexible tether engages the first ramp and is simultaneously disposed through the first aperture and the second aperture.

* * * * *